United States Patent [19]

Barritault et al.

[11] Patent Number: 5,852,004
[45] Date of Patent: Dec. 22, 1998

[54] DRUG AND PHARMACEUTICAL COMPOSITION FOR THE TREATMENT OF LESIONS OF THE DIGESTIVE TRACT

[75] Inventors: Denis Barritault, Paris; Jean-Pierre Caruelle, Saint Maur; Anne Meddahi, Creteil, all of France

[73] Assignee: Societe Valbiofrance, Creteil Cedex, France

[21] Appl. No.: 714,178

[22] PCT Filed: Mar. 29, 1995

[86] PCT No.: PCT/FR95/00399

§ 371 Date: Dec. 30, 1996

§ 102(e) Date: Dec. 30, 1996

[87] PCT Pub. No.: WO95/26737

PCT Pub. Date: Oct. 12, 1995

[30] Foreign Application Priority Data

Mar. 30, 1994 [FR] France .................................. 94 03804

[51] Int. Cl.[6] ........................ A61K 31/715; A61K 31/73; A61K 31/725; A61K 31/70

[52] U.S. Cl. ................................. 514/54; 514/55; 514/56; 514/57; 514/59; 514/62; 514/882; 514/925; 514/926; 514/927

[58] Field of Search .................................. 514/54, 55, 56, 514/57, 59, 62, 882, 925, 926, 927

[56] References Cited

U.S. PATENT DOCUMENTS 5,401,721   3/1995   Folkman et al. .......................... 514/12

OTHER PUBLICATIONS

CA 119:364, Morere et al., 1992.

*Primary Examiner*—Kimberly Jordan
*Attorney, Agent, or Firm*—Jacobson, Price, Holman & Stern, PLLC

[57] ABSTRACT

Use of at least one polymer or one biopolymer, called HBGFPPs, specifically protecting the growth factors of families of FGFs and beta TGFs from tryptic degradation and not significantly inhibiting coagulation, in the manufacture of a drug for the treatment of lesions of the digestive tract and of primary or secondary derived tissues of the endoderm and the mesoderm.

14 Claims, 6 Drawing Sheets

▲ FGF
○ FGF plus heparin
● FGF plus mesoglycan
△ FGF plus sulodexide

DAYS

○ FGF$_1$
● FGF$_1$ plus heparin
▲ FGF$_1$ plus mesoglycan
△ FGF$_1$ plus sulodexide

DAYS

△  FGF2
●  FGF2 plus heparin
▲  FGF2 plus mesoglycan
○  FGF2 plus sulodexide

DRUG AND PHARMACEUTICAL COMPOSITION FOR THE TREATMENT OF LESIONS OF THE DIGESTIVE TRACT

FIELD OF THE INVENTION

This invention relates to the use of polymers or biopolymers for the preparation of a drug for the treatment of lesions of all origins affecting the digestive tract from the buccal cavity to the anal extremity in human or veterinary medicine.

It also relates to a composition containing these polymers and intended for such a treatment.

BACKGROUND

The synthesis of CMDBS polymers (dextrans substituted by carboxymethyl, benzylamine and sulfonate) has been described in French Patent 2 461 724 and U.S. Pat. No. 4,740,594. Some of these polymers mimic heparin and may be used as plasma heparin replacement products, thanks to their anticoagulant and anticomplement properties.

Some of these CMDBS polymers mimic another property of heparin consisting of a stabilization, protection and potentialization of the in vitro biological activity of the growth factors of the FGF family (Tardieu and coll., Journal of Cellular Physiology, 1992, 150 pp. 194 to 203).

French Patent 2 644.066 describes the use of certain CMDBSs associated with FGFs for healing the skin and the cornea. Experiments have been conducted by provoking a cutaneous wound with the help of a hollow punch 6 mm in diameter in the rat. In this example, the CMDBS associated with the FGF 2 makes it possible to obtain a definite effect on the speed and the quality of skin repair.

Another biopolymer, dextran sulfate, has also been advanced in association with FGFS, as a stabilizer and protector, in Japanese Patent No. 13890. Dextran sulfate, moreover, is widely used in skin healing ointments and creams as well as in collyrium compositions, but, to the knowledge of the applicant, has no reported effect on the healing and regeneration of muscular lesions.

Another agent, sucrose sulfate ester and its aluminum salt, sucralfate, are products described and used, on their own or associated with FGFs, as agents in the treatment of ulcers and lesions of the digestive tract (U.S. Pat. No. 3.432.489) and in different pharmaceutical associations and compositions described in a series of patents (U.S. Pat. Nos. 4,975, 281, 4,885,281, 5,013,557, 5,164,379, 5,196,405, 5,240,710 and Danish Patents 102488 and 505588).

The tissues of the digestive tract are particularly rich in growth factors and several authors have described the presence and/or action of FGFs and beta TGFs in/on enterocyte cells or the healing action of these factors in lesions of tissues of the digestive tract as well as the presence or the action of growth factors presenting an affinity for heparin or heparan such as AB or BB PDGFs or Hepatocyte Growth Factor (Lemoine N R; Leung H Y; Gullick W J; Growth Factors in the Gastrointestinal tract ; Gut 1992, 33, pp. 1297 to 1300; Di Gulietta A, Hervada T; Nardy R V; LESH C A: Effect of platelet derived growth factor BB on indomethacin-induced gastric lesions in rats; Scand. J. Gastroenterol. 1992, 27, pp. 673 to 676; Tajagascu M and coll. Hepatocyte growth factor induces mitogenic reaction to the rabbit gastric epithelial cells in primary culture; Biochem. and Biophys. Res. Comm. 1993, 191; 528–534; Mustoe and Coll. Differential acceleration of healing of surgical incisions in the rabbit gastrointestinal tract by platelet derived growth factor and transforming growth factor beta; Surgery 1990, 108, pp. 324 to 330; Katayama M; Kan M: Heparin-binding (fibroblast) growth factors are potential autocrine regulators of oesophageal epithelial cell proliferation, In Vitro Cell. Dev. Biol. 1991, 27, pp.533 to 541).

It thus emerges from an analysis of the state of the prior art that polymers have already been used in association with growth factors on certain lesions of a very particular type of tissue, namely cutaneous tissue.

In view of the unpredictable nature of the therapeutic effects of a given molecule, it was not clear wether these polymers could have an effect on tissues other than those of the skin.

It is, in fact, well known that the different tissues of the human or animal body present structural and functional specific features making it impossible to predict the effect of a molecule, known for its effect on the cutaneous tissue, and on tissues of the digestive tract.

This is particularly true in view of the fact that the tissues of the digestive tract and those of cutaneous tissues, for example, have different embryonic origins.

Similarly, it is well known that it is impossible to predict the in vivo activity of a molecule on a particular tissue from results obtained in vitro on a specific experimental model.

All the other known drugs in this field, such as anti ulcerous drugs, act by protecting the mucosa by antacid gels, by inhibition of gastric acid secretions or by $H_2$ anti-receptor action.

The activity of a mixture of glycosaminoglycans, mesoglycan, on hemorrhoids has been tested by Saggioro et al., (1985, Min. Diet. e. Gastr, 31, pp. 311–315). This publication shows that mesoglycan is very effective against hemorrhoids, eliminating the symptoms while improving the endoscopic aspect.

However this publication teaches only its inquiry polymers of a very particular type which, moreover, present a composition of poorly defined animal origin and subject to variations.

SUMMARY OF THE INVENTION

Surprisingly, it has been found, according to the invention, that certain polymers have a very marked effect on the speed of healing and regeneration of lesions of digestive tract tissues as well as on the quality and solidity of these scars.

It has also been shown that very low doses of these polymers provide therapeutic effects.

This invention relates to the use of at least one polymer or one biopolymer, called HBGFPP, with the exception of mesoglycan, specifically protecting the growth factors of the FGF and beta TGF families from tryptic degradation and not significantly inhibiting coagulation, in the manufacture of a drug for the treatment of lesions of the digestive tract, and of secondary and primary derived tissues of the endoderm and the mesoderm.

In particular, such a polymer displays an anticoagulant activity of less than 50 international units per mg of polymer, measured according to Maillet et al. (Mol. Immunol, 1988, 25, 915–923). Advantageously, the polymer potentializes the FGFs in vitro.

Preferably, it does not substantially activate the complement system, that is to say, it possesses an anti-complement system of above 0.5 μg for the $CH_{50}$ (according to Mauzac et al., Biomaterials, 6, 61–63, 1985).

BRIEF DESCRIPTION OF THE DRAWINGS

According to the invention, polymers are understood to mean any natural substance, chemically modified natural substance or totally synthetic substance responding to the definition given above.

The following polymers are therefore concerned:

polymers obtained from dextrans but modified by other types of substitutions with other types of radicals, natural polymers other than those deriving from dextrans but including osidic residues (cellulose, chitin, fucanes, etc.), polymers obtained by polymerization of monomers of non-osidic nature (malic polyacid, oxalic polyacid, lactic polyacid, polystyrene, polyethylene glycol), whether or not modified.

Advantageously, the said polymer or biopolymer is a polysaccharide which may be principally composed of glucose residues.

It may also comprise glucosamine and/or uronic acid residues, particularly in the form of glucosamine dimer-uronic acid.

Such a polysaccharide advantageously displays a molecular weight of at least 10 kD and advantageously of about 40 kD.

This invention also relates to a pharmaceutical composition containing these polymers.

The polymers and/or biopolymers may be selected from natural substances which may then be modified, if required, by additions of appropriate chemical groups, or again be obtained entirely by synthesis. These natural, semi- or wholly synthetic polymers are then selected on the basis of their ability to interact specifically with several growth factors, notably those of the FGF and the beta TGF families. They are also selected on their ability to protect this (or these) factor(s) against proteolytic degradations. These polymers will be referred to under the generic abbreviation HBGFPP (heparin binding growth factor protectors and promoters). Two prototypes of these polymers or biopolymers are given as examples together with the processes and selection criteria of these polymers.

The first HBGFPP example belongs to the CMDBS family which are known products, namely functionalized biospecific dextrans, substituted by carboxymethyl, benzylamide and benzylamine sulfonate. These polymers illustrate the yielding of HBGFPPs from natural products (dextrans) which are subsequently chemically substituted. The second example describes the selection of wholly natural products, such as purified sulfate proteoglycosaminoglycans from tissular extracts.

These two examples illustrate the ability of these HBGFPPs to interact, stabilize, protect and potentialize the growth factors of the FGF and beta TGF families, and their use in a pharmaceutical composition permitting the protection, healing and/or regeneration of lesions of all origins affecting the digestive tract from the buccal cavity to the anal extremity.

In this patent application, by <<treatment>> is meant any curative or preventive operation carried out for the prophylaxis and the healing of lesions of the digestive tract, whether these lesions be of superficial or profound ulcerous type and whatever their origin, and/or the healing of perforations and/or surgical cuts and incisions as well as anastomoses performed on appropriate regions of the digestive tract.

A drug or a pharmaceutical composition according to the invention contains an effective amount of HBGFPP, for example CMDBS associated with one or more compatible and pharmaceutically acceptable vehicles. It may also be associated with agents such as, for example, anti-inflammatory, antibacterial, antifungal agents, gels, plasters, antacid dressings, $H_2$ anti-receptor agents or anti-proton pump agents used in the treatment of gastric ulcers, and agents commonly used in buccal or dental care or in the treatment of hemorrhoids.

Advantageously, such a composition is designed to be absorbed directly by oral route, deposited on the lesion or injected if the said lesion is directly accessible, notably in subcutaneous, buccal or rectal lesions, or again during surgical interventions by depositing or soaking the extremities of the tissues before restitching or repatching or carrying out anastomoses. The unit dose is from 10 to 2500 µg of CMDBS or HBGFPP per ml.

The vehicle may be physiological serum or buffers, such as PBS, containing 0.15M NaCl or any other compatible solution which does not irritate the damaged tissue. Formulations providing thick solutions or in gel or aerosol according to standard techniques known to the person of ordinary skill in the art may be proposed depending on the type and the accessibility of the lesion.

Thus, for directly accessible lesions, such as buccal aphthas, lesions of the tongue or the palatal vault, or of gums and all support tissues of teeth or of the throat, the composition may be applied in the form of a solution, suspension, spray, powder, gel, unguent or ointment, paste or gelatinous cream, toothpaste, dental fixative, periodontal implant, chewing gum, effervescent tablets or tablets to be sucked, and may also be applied by means of a little pipette, spatula or brush. The composition described in this invention has the effect of curing the lesions, whether these lesions are accidentally caused, as in the case of thermal or chemical cuts and burns of microbial, fungal or viral origin (provided that the cause of the lesion is also treated by associating antimicrobial, antifungal or antiviral agents), or whether the lesions are due to other origins which are not always identifiable or known, or lesions resulting from chemotherapy or radiotherapy.

Similarly, for anorectal lesions, diseases or irritations, the composition concerned by this invention provides a treatment which reduces the irritation, itching and swelling of the tissues, and the suffering caused by anorectal diseases, and leads to the curing of these lesions by favoring tissue repair and regeneration. The anorectal diseases involve the perianal regions, the anal canal and the rectum and include hemorrhoids of extremely varied origin such as constipation, diarrhea, pregnancy, anal infections, rectal carcinomas, and other disorders like anal fistulas and fissures which may have diverse causes sometimes induced by chemotherapy or radiotherapy. As with lesions of the upper passages of the digestive tract, anorectal lesions are directly accessible and the composition may be applied in the form of a solution, suspension, spray, powder, gel, unguent or ointment, paste or gelatinous cream, or a suppository and by using a pipette or syringe whose nozzle is introduced in the anal canal or a spatula, brush or any other appropriate means.

The composition may be associated with other compositions commonly used in the treatment of anorectal diseases which have been listed non exhaustively in a monograph, No. 45 35576 the May 26, 1980, published by the American Food and Drug Administration (FDA). This monograph describes over 75 ingredients, classified in families such as local anesthetics, vasoconstrictors, protectors, anti-irritants, astringent agents, healing agents, antiseptics, keratolytics and anticholinergics.

The results obtained by applying this composition are of a quite different order to those obtained with existing products including sucralfate-based compositions such as those described in U.S. Pat. No. 5,196,405 issued on the of Mar. 23, 1993 for the treatment of hemorrhoids or in U.S. patent application Ser. No. 52407010 (DK102488 and DK505588). Depending on the surface of the wound, the CMDBS or HBGFP product doses correspond to a fraction of an initial solution of 10 to 2500 ug per milliliter (which, for a local application on common wounds, implies a dose which is rarely above a few hundred microliters of solution), this dose being applied once or twice per 24 hours. The sucralfate compositions used are 0.01 to 5% (according to U.S. Pat. No. 5,196,405), in other words at least 10 times higher than those described in this invention, and the effects described in all the examples of the said U.S. Pat. No. 5,196,405 are obtained from 50 milligram per milliliter compositions.

For digestive tract lesions which are not easily accessible by topical route, the administration route of the composition is either oral or rectal. This HBGFP-based composition is effective in the treatment of lesions of the pharynx, the stomach, the esophagus, the duodenum, the small intestine and the colon. Mention may be made, as non exhaustive examples of lesions which may be treated with benefit by the HBGFP-based compositions concerned by this invention, of mucosa lesions of parts of the digestive tract provoking ulcers such as gastric acid or duodenal ulcers; lesions induced by drugs, by accidentally absorbed chemical products, or by treatments by radiation, lesions induced by stress or by foodstuffs, or of surgical or traumatic origin, viral lesions or those associated with inflammations such as hemorrhagic rectolitis, or Crohn's disease.

The stimulating activity of the reparation of digestive tract tissues may also be envisaged for other secondary and primary derived tissues of the endoderm and the mesoderm such as glandular derivatives, for example the liver, the pancreas, the salivary glands, the adenohypophysis, or pharyngeal and respiratory derivatives, for example bronchi, lungs, pleuras.

The HBGPPs may thus be recommended in the reparation of lesions of all origins affecting these other secondary and primary derived tissues of the endoderm and the mesoderm (traumatic lesion induced by surgery or by tumoral or other pathologies).

EXAMPLE 1

CMDBS preparation and selection a) CMDBS preparation

CMDBSs are dextrans substituted by carboxymethyl, benzylamide and benzylamide sulfonate groups. The method of synthesizing the CMDBSs may be that described by M. Mauzac and J. Josefonvicz in Biomaterials 1984, 5, pp 301–304.

According to this process, carboxymethyl dextran (CMD) is prepared from dextran by substituting several glycosylated units with carboxyl groups on the carbon in positions 5 and 6.

In the next phase, benzylamide is coupled with the carboxyl groups to form carboxymethyl-benzylamide dextran (or CMBD). Finally, a few aromatic nodes of benzylamide are sulfonated in order to yield carboxymethyl dextran benzylamide sulfonate or CMDBS.

The sodium salts of these derivatives are ultrafiltered, lyophilized and dissolved in the appropriate buffer prior to use.

Figure 1:
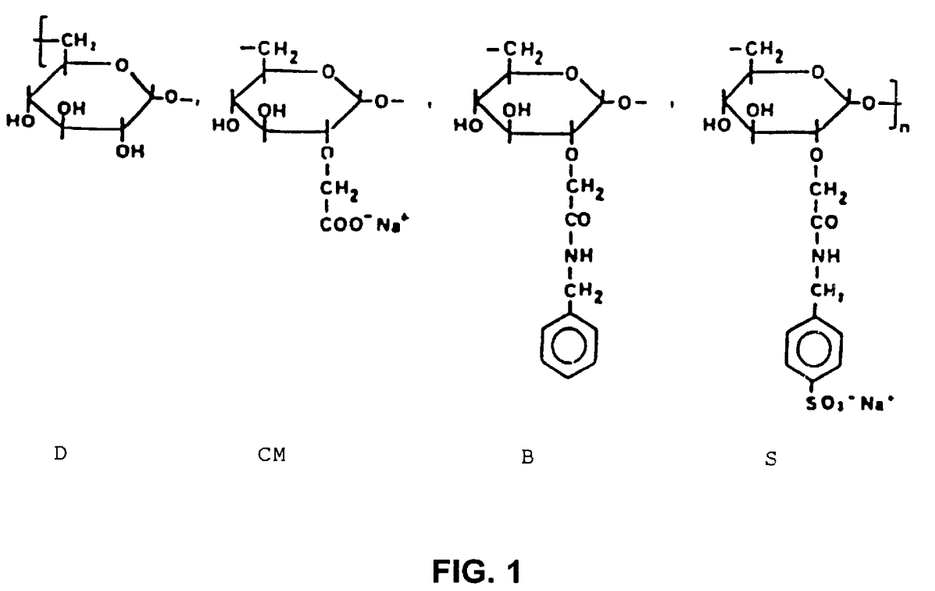
FIG. 1 represents the CMDBS formula.

The general formula of the CMDBSs is illustrated in FIG. 1.

The CMDBSs possess a statistical distribution of the different substituents. The percentages for each CMDBS type are determined by using standard methods.

b) CMDBS selection i: FGFs protection and stabilization tests

During the synthesis of the CMDBS the substitution rate of each of the groups may be controlled by modifying the substitution reaction conditions. Control of such parameters as temperature, reaction time, relative concentrations of the constituents, substitution reaction number, etc., makes it possible to obtain a very large number of substituted polymers. The substitution of the hydroxyls by carboxymethyl on the carbons in positions 5 and 6 gives carboxymethylation rates ranging from 0 to 200% (100% for each of the carbons in position 5 and 6). The carboxymethyl group may, in turn, be partially or totally used for fixing the benzylamide. The benzylamide groups may be partially or totally used for the sulfonation. The functionalized substituted dextrans used according to the invention are among those specifically described in French Patent 2.461.724. In addition to its ability to stabilize and protect FGF family growth factors, as described in the publication of Tardieu et coll., J. Cell. Physio. 1992, 150, pp 194 to 203 and in French Patent 2.461.724, the selected CMDBS must be able to interact with at least one member of the growth factors family belonging to the beta TGF family according to an evaluation method described below, and to protect the beta TGFs against proteolysis.

ii. Evaluation of the interaction capacities between CMDBS and beta TGF family growth factors.

In order to measure the capacity of certain CMDBSs to interact with members of the beta TGF family and, by means of this interaction, to protect the beta TGFS, a grading test was devised. This test consists in measuring the ability of the selected CMDBS to allow the beta TGF to maintain its biological activity despite a protease treatment.

In the example below, the CMDBS used is batch 26.2 defined by a substitution rate of 110% of carboxymethyl units, 3.6% of benzylamide units and 36.5% of sulfonate units, and possesses an anticoagulant activity of 4 IU/mg (International Units). This batch's anticomplement activity is 1.1 µg of $CH_{50}$ measured according to Mauzac et al. (previously cited).

The heparin used as control was supplied by the Sanofi company (Choay Institute) and presents an anticoagulant activity of 175 IU/mg.

The beta 1 TFG is prepared from human blood platelets according to a protocol described in numerous publications (for example Growth factors and their receptors, 1992, vol 1 pp 419–472, written by A. Roberts and M. Sporn, edited by A. Roberts and M. Sporn, and published by Springer Verlag Berlin) and is commonly used by persons of ordinary skill in the art. The beta TGF biological activity test used in this example is that of the inhibition of CCL64 cells (from the American Tissue Culture Collection). This inhibition is measured by the ability of the beta TGF to inhibit the incorporation of tritiated thymidine in a dose dependent manner in these CCL64 cells stimulated by the FGF or by fetal calf serum according to the protocol described by Van Zolen in Progress in Growth Factor Research, 1990, 2, pp 131 to 152. Two doses of beta TGF are used, one corresponding to the 50% inhibition capacity of the incorporation of tritiated thymidine (defined as the inhibiting activity unit) and the other corresponding to the 100% inhibition capacity. In this example, the values obtained are 250 pg of TGF for the CCL64 cells cultivated in 1 ml of culture medium.

A 50 ng sample of beta TGF in saline phosphate buffer containing 0.1% bovine albumin serum (from the SIGMA company, Saint Louis USA) is incubated on its own, or associated either with 5000 µg of CMDBS or 5000 µg of heparin, with or without 500 µg of trypsin. The final volume of the incubated solution is adjusted to 1 ml and incubation is carried out at 37° C. for a varying length of time (10 minutes in the example described (Table 1)).

20 µl samples of a volume of are taken from each of the incubation reactions and added to CCL64 cells cultivated in 24-well plates, each well containing one milliliter of culture medium according to the aforementioned protocol described by E. Zohlen. In these conditions, the final concentration of beta TGF per well is 1 ng/ml. Table 1 summarizes the results obtained in various conditions and shows the protective effect of the CMDBS. Thus, after 10 min of incubation at 37° C., 75% of the biological activity of the beta TGF is still present, whereas heparin, despite the fact that it can be fixed to the beta TGF (Mac Caffrey et al., J of Cell. Physiology, 1992, vol 52, pp 430–440), does not protect the beta TGF against this proteolytic degradation (less than 20% of biological activity remain). It should be remembered that, in the case of FGFs, heparin provides protection against proteolysis induced by trypsin (Tardieu et al., Journal of Cellular Physiology, 1992, 150: pp. 194–203).

It was verified that the CMDBS had no inhibiting power on the activity of trypsin (Table 2). Thus, 10 µg of trypsin were incubated, either with a substrate (S.87 supplied by the Serbio company in Paris and used according to the supplier's recommendations) or with this substrate and a trypsin inhibitor such as that originating from soya (such as the soybean trypsin inhibitor or STI from Sigma), these incubations being carried out in the absence or presence of varying quantities of CMDBS (batch AM26). The enzymatic activity of trypsin was measured by spectrophotometric absorption of the transformation product of S 87 versus incubation time.

EXAMPLE 2

Selection of other HBGFPPs

A commercial preparation of proteoglycosaminoglycan and glycosaminoglycans, sulodexide, was selected according to its ability to interact with the growth factors of the FGF and beta TGF families.

Preparations of heparan sulfate obtained by fractionating mesoglycan and sulodexide were also tested.

The mesoglycan and sulodexide were supplied by the Sigma Chemical Co, Saint Louis Mo. USA. Their properties are summarized in Table 3.

The cells used in this example are CCL39 cells from the American Tissue Culture Collection. The conditions concerning culture and the measurement test of FGF biological activity are the same as those described in the publication by Tardieu and coll. in the Journal of Cellular Physiology, 1992. The FGF growth factors used are the FGF 1 and FGF 2 recombinant forms.

a) Effect of sulodexide on the in vitro biological activity of the FGFs

In these experiments, the FGF 1 or 2 is used at a dose corresponding to the effective dose (indicated $ED_{50}$) in order to induce a stimulation of the biological activity of 50% of the dose inducing the maximum stimulation. The biological activity is measured by the ability to induce an increase of the incorporation of tritiated thymidine in the cells according to protocols extensively described in numerous publications such as the previously mentioned publication by Tardieu et coll. and also in French Patent 2 644 066.

Figure 2:
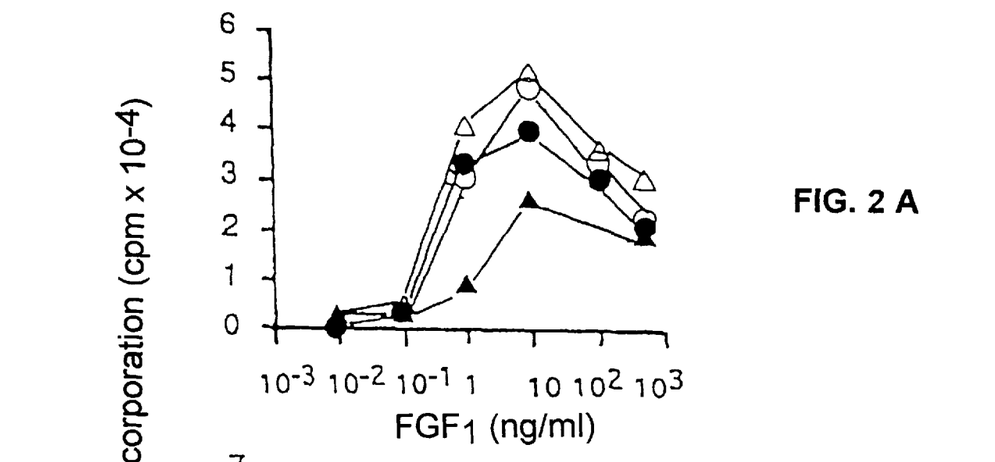
FIGS. 2A and 2B illustrate the potentialization of the biological activity of FGF1 (2A) and FGF2 (2B) by heparin, mesoglycan and sulodexide. Biological activity is measured on CCL39 cells by measuring the increased incorporation of tritiated thymidine versus the dose of FGF1 and FGF2 added alone or in the presence of 20 µg of heparin, 10 µg of mesoglycan or 10 µg of sulodexide.
Figure 3A:
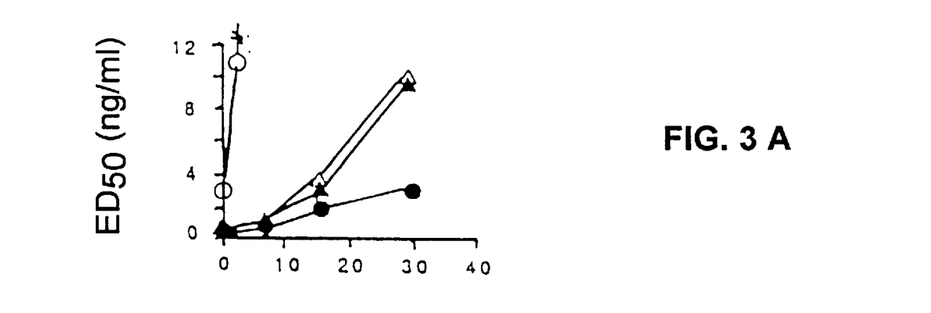
FIGS. 3A, 3B, 4A and 4B illustrate the protective effect of heparin, mesoglycan and sulodexide against a thermal degradation of FGF1 (3) and FGF2 (4) . FGF samples are incubated on their own or in the presence of 20 pg of heparin, 10 µg of mesoglycan or 10 µg of sulodexide at 20° C. (a) and 37° C. (b) for 1, 7, 15, 30 days. The measurement of the biological activity presented in abscissa corresponds to the stimulation unit values ($ED_{50}$) of the incorporation of tritiated thymidine in CCL39 cells.
Figure 3B:
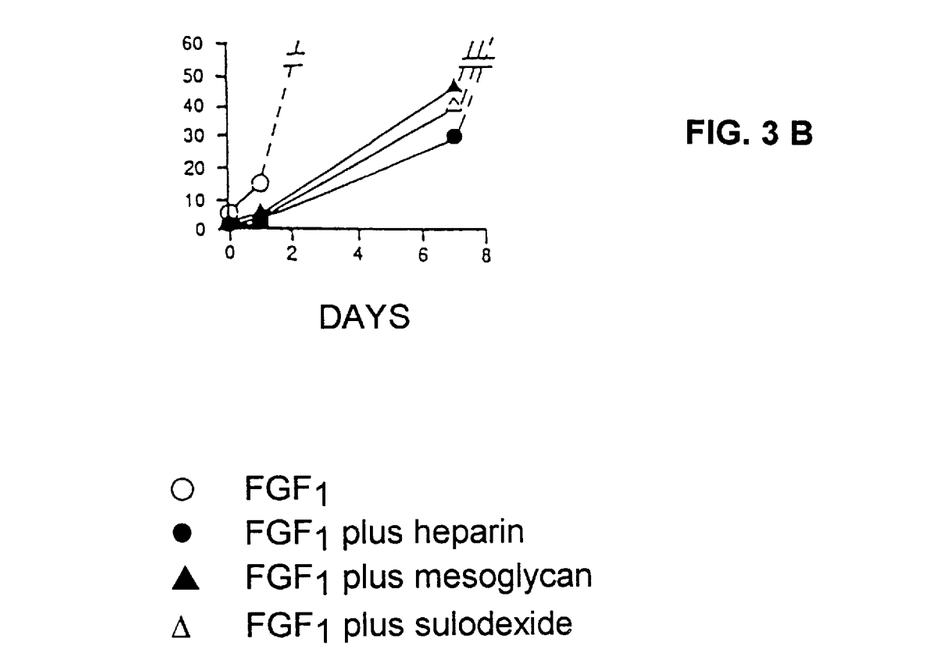
Figure 4:
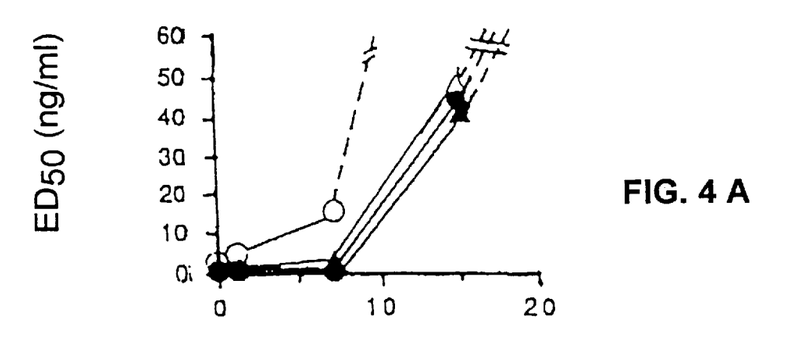
Figure 5:
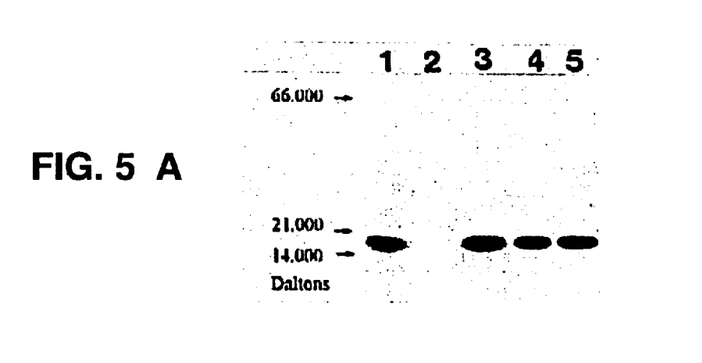
FIG. 5A illustrates the protective effect of heparin, mesoglycan and solodexide against a proteolytic degradation of the $^{125}$I-FGF1. Proteolytic digestion was carried out at 37° C. and the samples were separated by 18% polyacrylamide gel electrophoresis. The gels are dried and autoradiographed. The first track contains the 125I-FGF1 on its own. The $^{125}$-FGF1 is incubated in the presence of trypsin (track 2), heparin (track 3), mesoglycan (track 4) or sulodexide (track 5).
FIG. 5B illustrates the protective effect of heparin, mesoglycan and sulodexide against a proteolytic degradation of the $^{125}$I-FGF2. The arrangement of the tracks is identical to that presented for the $^{125}$I-FGF1 in FIG. 5A.

In this example, the $ED_{50}$ is 5 ng/ml for the FGF 1 and 3 ng/ml for the FGF 2, these values being measured experimentally (FIG. 2A and 2B).The same stimulation experiment in function of the FGF dose is carried out in the presence of 10 µg/ml of sulodexide, or 20 µg/ml of heparin. FIG. 2 shows that in these conditions the $ED_{50}$ becomes 0.4 ng/ml and 0.2 ng/ml respectively for FGF 1 and FGF 2 in the presence of these doses of sulodexide or heparin. In addition to this ability to potentialize the biological activity of the FGFs, the HBGFPPs protect the FGFs against thermal degradations and the inactivation induced by the proteolytic action of trypsin (FIGS. 4 and 5). Similarly, these HBGFPPs protect FGF1 and 2 against an inactivation induced by the proteolytic activity of trypsin (FIGS. 5A and 5B).

b) Protective effects of sulodexide, dextran, dextran sulfate and sucrase with regard to beta TGFs.

Several other compounds were evaluated: dextran sulfate (Sigma Chemical, molecular weight 40.000, the dextran having been used for the synthesis of the CMDBS (also from Sigma)), sucrase or sucrose octasulfate (supplied by D. Bar Shalom, Bukh Medic company, Denmark). Some of these compounds were chosen because they protect and stabilize FGFs, for example sucrase (see. U.S. Pat. No. 5,202,311) or dextran sulfate (see. Japanese Patent 138 907/88). The dextran is the one used in the synthesis of CMDBS AM26.

The protection experiment of the beta TGF biological activity was carried out in the same way as with the CMDBS as described in Example 1 ii. The incubation mixture contained 50 ng of beta TGF (in 0.1% bovine serum albumin) and trypsin (500 µg). Mesoglycan or sulodexide or dextran sulfate or dextran or sucrase are used at the dose of 5000 µg.

The beta TGF biological activity is measured as described above after a dilution of 50 times and by using CCL64 cells.

The results are presented in Table 4.

These results show that, like certain CMDBSs capable of responding to the two selection criteria with regard to the FGFs and beta TGFs, sulodexide presents a significant protective activity for the beta TGFs.

c) Isolation of the heparan sulfate fraction of sulodexide and mesoglycan

Sulodexide and mesoglycan correspond to mixtures of several substances essentially made up of different glycosaminoglycans (GAG).

By means of a first purification stage, it was established that a gram of dry product of each of these two products contained respectively 874 mg for the mesoglycan and 795 mg for the sulodexide of total GAGs.

This purification was obtained by subjecting these solubilized products to ion exchange chromatography (DEAE-Trisacryl) in order to remove all proteic contaminants. The total GAGs were then purified by eluting the DEAE gel with a sodium acetate solution, pH 4, containing 1.5M NaCl.

After an extensive dialysis phase against water, 60 mg of each product of GAG are digested by the ABC chondroitinase overnight at 37° C. (1 unit per mg of GAG). This enzyme degrades all the GAGs with the exception of the heparan sulfates (HS). The products of digestion were subjected to molecular sieve chromatography (G50 Sephadex, 1.8×95 cm column). Elution was then carried out on ammonium bicarbonate buffer at a rate of 18 ml/hour. The non digested material corresponding to HS-type GAGs was collected in the elution dead volume of the column.

The GAG concentrations were calculated from their uronic acid content using the carbazol method (Bitter T. and Muir H. M., 1962, Anal. Biochem 4, pp. 330–334).

From these measurements the following composition of each of the products was obtained:

|  | Sulodexide | Mesoglycan |
| --- | --- | --- |
| Total GAGs | 79% | 87% |
| Heparan Sulfate Fraction (HS) | 48% | 52% |
| Other GAGs | 31% | 35% |

The HS fractions of each of these two products were again chromatographed on a DEAE Trisacryl gel. 1 mg of each HS fraction, purified with mesoglycan (FIG. 6A) or sulodexide (FIG. 6B) in 3 ml, was deposited on a balanced column with 0.05M NaCl buffer, 0.05M TMS-Hcl pH 7.5. After washing of the column with 10 volumes of the same buffer followed by washing with 10 volumes of 0.05M NaCl buffer, 0.05M of sodium acetate pH 4, the material fixed to the column is desorbed by a saline gradient ranging from 0.05M NaCl to 1.5M NaCl in the same acetate buffer. 1 ml of each fraction collected was measured by the carbazole method.

Figure 6:
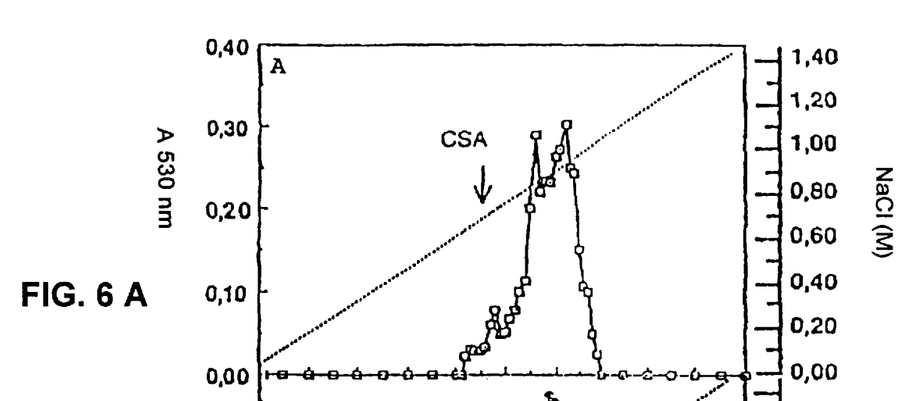
FIGS. 6A and 6B are DEAE-Trisacryl column elution profiles, respectively, of HSM fractions (FIG. 6A) and HSS fractions (FIG. 6B) in the presence of chondroitin sulfate (CSA) fractions for the calibration of the column.

The material corresponding to the HS constituents of each of the original products shows approximately the same elution profile and thus roughly the same apparent load. This elution peak maximum is obtained for a saline concentration of 0.94M NaCl. A defined fraction of chondroitine sulfate (CSA) was subjected to the same protocol in order to calibrate chromatography. This CSA fraction, containing only one sulfate group by disaccharide, is eluted at the ionic strength of 0.72M NaCl.

These results show that the HS fraction contains more sulfate groups than the reference CSAs. The HS fraction presents about two sulfate groups per dissacharidic unit.

These fractions were tested in order to discover their protective power with regard to the beta TGF and the FGF compared to the powers established with the respective raw products.

Semi-quantitative evaluation of the FGF protective effects of the FGF by different polymers As described above, a constant quantity of radioactive FGF is incubated under various conditions. After autoradiography of the reaction products, the non degraded quantity of radioactive FGF is quantified by densitometry. The values correspond to the percentage of radio-labelled FGF found compared to the quantity deposited at the start of reaction (Table 5).

The results of Tables 4 and 5 show that the HSM and HSS fractions, originating respectively from mesoglycan and sulodexide, show protective effects which are greater than these two compositions and are close to 100%.

EXAMPLE 3

In vitro Inhibiting effects of CMDBSs and glycosaminoglycans on the activity of leukocytic elastase and plasmin The inhibiting powers of different CMDBS and of the intermediate compounds of their synthesis were established for leukocytic elastase and plasmin.

The purified leukocytic elastase was obtained by Elastin Products Co (Owenville, Mo., USA) and the plasmin from SIGMA.

The inhibition of enzymatic activities by these different compounds is carried out at 37° C. in a thermostatic bath. The enzymes under consideration are placed in solution in a 100 mM Tris-HCL buffer, pH 8 for the elastase and pH 7.4 for the plasmin, in the presence of 0.02% sodium azide and 0.01% Triton X100 for the plasmin. The substrate and enzyme concentrations are: 0.10 mM MeO-Suc-Ala-Ala-Pro-Val-pNA (paranitroanilide) for the elastase at 8.3 nM, and 0.20 mM dVal-Leu-dLys-pNA for the plasmin at 77 nM. The $IC_{50}$ is determined for each of the conditions.

Table 6 gives the results obtained, in which batch AM6 corresponds to a T40 dextran of 40,000 kD. Batch EM5 corresponds to a T10 dextran of 10,000 kD. The intermediate products of synthesis are identified by the symbols given above with an index number specifying the number of each substitution reaction.

The $IC_{50}$ values show that the CMDBSs have non competitive hyperbolic-type inhibiting effects on leukocytic elastase activity which are comparable to those of heparin, one of the best inhibitors of this activity (Ki of the order of 1 nM). In addition, and unlike heparin, the CMDBSs show inhibiting effects on plasmin.

Table 6 also shows that the inhibiting effects of the HSM and HSS fractions are greater than those of mesoglycan and sulodexide, respectively.

EXAMPLE 4

Healing effect of CMDBS on anastomosis of the colon

The batch of CMDBS used in this example is that described in Example 1. A 50 µg per ml solution of CMDBS is made in a physiological serum. Male Wistar rats (Wi/Wi, Ico, Iffa Credo France), weighing 250 to 300 g are anesthetized with sodic pentobarbital. A subumbilical midline laparotomy is performed over 1.5 cm. The rectocolic junction is individualized and then sectioned with bistoury. The two banks of the anastomosis are then imbibed with a solution containing either the CMDBS or a physiological buffer for a period of two minutes. The anastomosis is carried out according to a termino-terminal mode in a plane by five separate stitches of polyglactine 910 thread, diameter 6/0. The knots are made of 6 loops. Parietal closure is performed in two planes. The rats are divided into two groups of 7 rats. The experiments are conducted in double blind. Samples are taken on the 2nd, 4th and 7th days after the operation. The quality of the healing is studied by measuring the rupture pressure of the anastomosis, in millimeters of mercury. The colon is sectioned 2 cm on either side of the anastomosis, one end being connected to a self-pushing syringe which injects water at a low, constant rate, and the other end being linked to a manometer. Pressure is recorded continuously on a reel of paper. The rupture pressure is determined by analyzing the tracing. The values obtained are presented in Table 7 below.

Results: At Day 2 (48 hours after the operation) a very marked difference greater, by the order of three times, is measured between the anastomosis rupture forces realized with and without CMDBS treatment. This mean is statistically significant ($p \leq 0.05$). At Day 4 this difference is much smaller and corresponds to an increased resistance of about 10% in favor of the animals treated with CMDBS. At Day 7, there is no longer any difference between the treated and untreated resistances. The benefit of the CMDBS treatment is clearly apparent since it provides a greatly improved anastomosis solidity at the crucial moment, that is to say at the very start of healing, for the risks of anastomosis rupture always occur in the first few days.

EXAMPLE 5
Healing effect of the CMDBS on colitis induced by acetic acid

Groups of 6 Sprague Dawley male rats weighing approximately 200 g are placed in hydric fasting 24 hours before the test. On the day of the test, the animals are anesthetized with pentobarbital (30 mg/kg) by intraperitoneal route. After laparotomy, a colic instillation of 2 ml of 5% acetic acid is performed 2 cm from the caecum. The acetic acid is left in contact for 10 seconds and the colon is then rinsed by 3 ml of saline phosphate buffer (PBS) at pH 7. The wound is then closed. The animals are sacrificed 72 hours later by cervical elongation. The colic alterations are noted on the following scale:
0: normal colon
1: congestion
2: superficial necrosis of the mucosa
4: major necrosis of the mucosa with edema
5: perforation
Treatment A first control group of six rats does not receive treatment.

A second group receives 50 μg of an aqueous solution of CMDBS (batch AM26), administered orally morning and evening for three days.

A third group receives sucralfate (marketed under the name of ULCAR Pharmaceutical Laboratories Fabre). The supplier's recommended dose is used (500 mg/kg, i.e. 100 mg per rat) administered orally twice a day for three days.
Statistical analysis The mean and the standard error were calculated for each batch of animals. Statistical comparison is performed using White's non parametric test compared to the control.

The results are presented in Table 8 below.

As these results show, the CMDBS reduces the seriousness of the colic lesions induced by acetic acid by about 75% (significant effect, $p \leq 0.05$). In contrast, the sucralfate has no significant effect on the healing of these ulcers.

EXAMPLE 7
HBGPP-based compositions

In examples 5 and 6 described above, the CMDBS is a buffered saline aqueous solution (PBS buffer) or physiological serum at concentrations of 50 μg/ml. Administration is local or per os; it may be intravenous. Other compositions may be proposed provided that the dose of CMDBS reaching the site of the lesion lies between 1 μg and 1000 μg.

TABLE 1

Protective effects of CMDBS and heparin against beta TGF degradation by trypsin

| incubation mixture at 37° C. for 10 min and containing, per milliliter, according to the indication: CMDBS or heparin (5000 μg): βTGF (50 ng): trypsin (500 μg) | % inhibiting activity of the incorporation of tritiated thymidine in CCL64 cells (after dilution 50 times of incubation mixture) |
|---|---|
| Incubation buffer only | 0 |
| CMDBS (5000 μg) | 0 |
| Heparin (5000 μg) | 0 |
| Trypsin (1000 μg) | 0 |
| Beta TGF (50 ng) | 100 |
| Beta TGF + CMDBS (batch AM26) | 100 |
| Beta TGF + heparin | 100 |
| Beta TGF + trypsin | 5 |
| Beta TGF + CMDBS + trypsin | 75 |
| Beta TGF + heparin + trypsin | 10 |

TABLE 2

Non inhibiting effect of CMDBS on trypsin

| Trypsin (10 ug/ml) + S87 | 100 |
|---|---|
| Trypsin + S87 + 5 μg/ml CMDBS | 100 |
| Trypsin + S87 + 50 μg/ml CMDBS | 100 |
| Trypsin + S87 + 500 μg/ml CMDBS | 100 |
| Trypsin + S87 + STBI | 0 |

TABLE 3

Origin, anticoagulant activity and partial composition of mesoglycan and sulodexide (supplier's information)

|  | Sulodexide | Mesoglycan |
|---|---|---|
| Origin | pig duodenum | Aorta |
| Anticoagulant activity | 50–70 IU/mg | <50 IU/mg |
| Chemical composition |  |  |
| Dermatan sulfate | 20–35% | 25–60% |
| Chondroitine sulfate | 2–7% | 3–15% |
| Heparan sulfate | + | + |

TABLE 4

Protection of the beta TGF by various polymers

| Beta TGF | 100% |
|---|---|
| Beta TGF + trypsin | 0% |
| Beta TGF + mesoglycan | 100% |
| Beta TGF + mesoglycan + trypsin | 50% |
| Beta TGF + HSM | 100% |
| Beta TGF + HSM + trypsin | 75% |
| Beta TGF + sulodexide | 100% |
| Beta TGF + sulodexide + trypsin | 20% |
| Beta TGF + HSS | 100% |
| Beta TGF + HSS + trypsin | 45% |
| Beta TGF + dextran | 100% |
| Beta TGF + dextran + trypsin | 0% |
| Beta TGF + dextran sulfate | 100% |
| Beta TGF + dextran sulfate + trypsin | 0% |
| Beta TGF + sucrase | 100% |
| Beta TGF + sucrase + trypsin | 0% |

HSM = Heparan sulfates purified from mesoglycan
HSS = Heparan sulfates purified from sulodexide

TABLE 5

Protection of the FGF by various polymers

|  | PROTECTION (in %) |
|---|---|
| FGF alone | 100% |
| FGF + trypsin | 0% |
| FGF + trypsin + heparin | 100% |
| FGF + trypsin + mesoglycan | 75% |
| FGF + trypsin + sulodexide | 70% |
| FGF + trypsin + heparinase treated mesoglycan | 0% |
| FGF + trypsin + heparinase treated sulodexide | 0% |
| FGF + trypsin + heparinase treated heparin | 0% |
| FGF + HSM + trypsin | 95% |
| FGF + HSS + trypsin | 90% |

TABLE 6

Inhibition of elastase and plasmin activities

| Tested compounds | Leukocytic elastase $IC_{50}$ in μg/ml | plasmin $IC_{50}$ in μg/ml |
|---|---|---|
| CMDBS, batch AM6 | 2.2 | 1.5 |
| T40 | >100 | >100 |
| CMDBS, batch EM5 | 10 | 7 |
| T10 CMD2B | 50 | 53 |
| T10 5CMD1B | >100 | >100 |
| T10 3CMD | >100 | >100 |
| T10 | >100 | >100 |
| Mesoglycan | 72 | 65 |
| HS mesoglycan | 20 | 22 |
| Sulodexide | 79 | 75 |
| HS sulodexide | 25 | 20 |
| Heparin | 1.8 |  |
| Lipo-heparin |  | 0.5 |

HSM = Heparan sulfates purified from mesoglycan
HSS = Heparan sulfates purified from sulodexide

TABLE 7

Study of the healing of the rectocolic junction

|  | DAY 2 | | DAY 4 | |
|---|---|---|---|---|
|  | CONTROLS | CMDBS | CONTROLS | CMDBS |
| Rupture pressure in | 38 | 48 | 112 | 136 |
| mm of Hg | 20 | 96 | 140 | 140 |
|  | 18 | 76 | 140 | 148 |
|  | 35 | 53 | 121 | 144 |
|  | 20 | 82 | 98 | 156 |
|  | 18 | 66 | 108 |  |
|  |  | 50 |  |  |
| mean | 22.45 | 67.28 | 119.8 | 144.8 |
| S.D. | 8.33 | 16.87 | 15.77 | 6.88 |
| n | 6 | 7 | 6 | 5 |

TABLE 8

Effect of CMDBS on colitis induced by acetic acid

| Treatment | Alteration score |
|---|---|
| Controls | 2.83 ± 0.48 |
| CMDBS 50 μg/rat per os | 0.70 ± 0.37 |
| Sucralfate 100 mg/rat per os | 2.25 ± 0.48 |

We claim:

1. A method of treating a lesion of the digestive tract or of primary or secondary derived tissue of the endoderm or the mesoderm, which comprises administering to a human or other animal in need of such treatment an effective amount of a pharmaceutical composition containing a) at least one polymer or one biopolymer, called HBGFPP, with the exception of mesoglycan, specifically protecting the growth factors of families of FGFs and beta TGFs from tryptic degradation and not significantly inhibiting coagulation, in association with b) at least one pharmacologically acceptable excipient.

2. A method according to claim 1, wherein the polymer or biopolymer presents an anticoagulant activity of less than 50 international units per mg of polymer.

3. A method according to claim 1, wherein the said polymer does not substantially activate the complement system.

4. A method according to claim 1, wherein the said polymer potentializes in vitro the FGF.

5. A method according to one of claim 1, wherein the said polymer substantially inhibits the proteasic activities of elastase and/or plasmin.

6. A method according to one of claim 1, wherein the said polymer or biopolymer is a polysaccharide.

7. A method according to claim 6, wherein the said polysaccharide is primarily composed of glucose residues.

8. A method according to claim 6, wherein the polysaccharide comprises glucosamine and/or uronic acid residues.

9. A method according to claim 8, wherein the polysaccharide comprises glucosamine-uronic acid dimers.

10. A method according to claim 8, wherein the said polysaccharide is a glycosaminoglycan, or a sulfate of one of these compounds, possibly associated with a lipid, a peptide or a protide.

11. A method according to claim 1, wherein the said polysaccharide is a substituted dextran.

12. A method according to claim 11, wherein the said polysaccharide is a CMDBS.

13. A method according to claim 1, wherein the said polymer is of non-osidic nature.

14. A method according to claim 1 wherein a) is the sole essential active component for treating a lesion of the digestive tract or lesion of primary or secondary derived tissue of the endotherm or of the mesoderm.

* * * * *